(12) United States Patent
Chen et al.

(10) Patent No.: US 9,523,646 B2
(45) Date of Patent: Dec. 20, 2016

(54) WAFER AND RETICLE INSPECTION SYSTEMS AND METHODS FOR SELECTING ILLUMINATION PUPIL CONFIGURATIONS

(71) Applicant: KLA-Tencor Corporation, Milpitas, CA (US)

(72) Inventors: Grace H. Chen, Los Gatos, CA (US); Rudolf Brunner, Mountain View, CA (US); Lisheng Gao, Saratoga, CA (US); Robert M. Danen, Pleasanton, CA (US); Lu Chen, Beijing (CN)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/158,413

(22) Filed: May 18, 2016

(65) Prior Publication Data

US 2016/0266047 A1    Sep. 15, 2016

Related U.S. Application Data

(63) Continuation of application No. 14/381,315, filed as application No. PCT/US2013/028650 on Mar. 1, 2013, now Pat. No. 9,347,891.

(Continued)

(51) Int. Cl.
*G01N 21/00* (2006.01)
*G01N 21/88* (2006.01)
*G01N 21/95* (2006.01)

(52) U.S. Cl.
CPC ...... *G01N 21/8806* (2013.01); *G01N 21/9501* (2013.01); *G01N 2021/8822* (2013.01);
(Continued)

(58) Field of Classification Search
CPC ............. G01N 21/956; G01N 21/9501; G01N 21/95607; G01N 21/8806; G01N 2021/151; G01N 2021/95615; G01N 21/21; G01N 21/33; G01N 21/55; G01N 2201/06113; G01N 2201/1035; G01N 21/95623; G01N 2021/95676
See application file for complete search history.

(56) References Cited

U.S. PATENT DOCUMENTS 9,347,891 B2    5/2016    Chen et al.
2004/0119973 A1*    6/2004    Fukuhara ............ G03F 7/70133
                                            356/239.2

(Continued)

FOREIGN PATENT DOCUMENTS

JP       H07333164 A    12/1995
KR    1020100069503 A     6/2010
(Continued)

OTHER PUBLICATIONS

U.S. Appl. No. 14/381,315, Non Final Office Action mailed Sep. 14, 2015, 12 pgs.
(Continued)

*Primary Examiner* — Michael P Stafira
(74) *Attorney, Agent, or Firm* — Kwan & Olynick LLP

(57) ABSTRACT

In an optical inspection tool, an illumination aperture is opened at each of a plurality of aperture positions of an illumination pupil area one at a time across the illumination pupil area. For each aperture opening position, an incident beam is directed towards the illumination pupil area so as to selectively pass a corresponding ray bundle of the illumination beam at a corresponding set of one or more incident angles towards the sample and an output beam, which is emitted from the sample in response to the corresponding ray bundle of the incident beam impinging on the sample at the corresponding set of one or more incident angles, is detected. A defect detection characteristic for each aperture position is determined based on the output beam detected for each aperture position. An optimum aperture configuration is determined based on the determined defect detection characteristic for each aperture position.

27 Claims, 9 Drawing Sheets

Related U.S. Application Data

(60) Provisional application No. 61/607,588, filed on Mar. 7, 2012.

(52) U.S. Cl.
CPC ............. *G01N 2201/061* (2013.01); *G01N 2201/0638* (2013.01); *G01N 2201/12* (2013.01)

(56) References Cited

U.S. PATENT DOCUMENTS

| | | |
|---|---|---|
| 2005/0001176 A1 | 1/2005 | Loney et al. |
| 2006/0262297 A1* | 11/2006 | Matsui ................. G01N 21/956 356/237.5 |
| 2007/0070336 A1* | 3/2007 | Maeda ............... G01N 21/8806 356/237.2 |
| 2011/0249112 A1 | 10/2011 | Endo |
| 2015/0015874 A1 | 1/2015 | Chen et al. |

FOREIGN PATENT DOCUMENTS

| | | |
|---|---|---|
| WO | 2010095420 A1 | 8/2010 |
| WO | 2013134068 A1 | 9/2013 |

OTHER PUBLICATIONS

U.S. Appl. No. 14/381,315, Notice of Allowance mailed Jan. 21, 2016, 8 pgs.
Int'l Application Serial No. PCT/US2013/028650, Preliminary Report on Patentability mailed Sep. 18, 2014, 10 pgs.
Int'l Application Serial No. PCT/US2013/028650, Search Report mailed May 30, 2013, 4 pgs.

* cited by examiner

WAFER AND RETICLE INSPECTION SYSTEMS AND METHODS FOR SELECTING ILLUMINATION PUPIL CONFIGURATIONS

CROSS-REFERENCE TO RELATED APPLICATION

This application is a continuation of and claims the benefit under 35 U.S.C. §120 of U.S. application Ser. No. 14/381,315, entitled WAFER AND RETICLE INSPECTION SYSTEMS AND METHODS FOR SELECTING ILLUMINATION PUPIL CONFIGURATIONS, filed 27 Aug. 2014 by Grace H. Chen et al., now issued as U.S. Pat. No. 9,347,891 on May 24, 2016, which is a U.S. national application under U.S.C. 371 of PCT Application Number PCT/US13/28650, entitled WAFER AND RETICLE INSPECTION SYSTEMS AND METHOD FOR SELECTING ILLUMINATION PUPIL CONFIGURATIONS, filed 1 Mar. 2013 by Grace H. Chen et al., which claims priority of U.S. Provisional Patent Application No. 61/607,588, entitled METHODS AND APPARATUS TO OPTIMIZE THE ILLUMINATION AND COLLECTION CONFIGURATION OF AN OPTICAL IMAGE BASED INSPECTION SYSTEM, filed 7 Mar. 2012 by Grace Chen et al. Both applications are herein incorporated by reference in their entireties for all purposes.

TECHNICAL FIELD OF THE INVENTION

The invention generally relates to a field of wafer and reticle inspection. More particularly the present invention relates to illumination pupil aperture optimization for inspection tools.

BACKGROUND

Generally, the industry of semiconductor manufacturing involves highly complex techniques for fabricating integrating circuits using semiconductor materials which are layered and patterned onto a substrate, such as silicon. An integrated circuit is typically fabricated from a plurality of reticles. Due to the large scale of circuit integration and the decreasing size of semiconductor devices, the reticles and fabricated devices have become increasingly sensitive to defects. That is, defects which cause faults in the device are becoming increasingly smaller. The device can generally be required to be fault free prior to shipment to the end users or customers.

Various inspection systems are used within the semiconductor industry to detect defects on a semiconductor reticle or wafer. In certain applications, the inspection system includes configurable illumination pupil configurations, as well as configurable imaging pupil configurations.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of facilitating an inspection of a sample using an optical inspection tool is disclosed. An illumination aperture is opened one at a time at each of a plurality of aperture positions of an illumination pupil area, and the aperture positions are spread across the illumination pupil area. While an illumination aperture is opened at each aperture position, an incident beam of the inspection tool is directed towards the illumination pupil area and this illumination aperture then manipulates the incident beam so as to selectively pass a corresponding ray bundle of the incident beam at a corresponding set of one or more incident angles towards the sample. An output beam, which is emitted from the sample in response to the corresponding ray bundle of the incident beam impinging on the sample at the corresponding set of one or more incident angles, is then detected. A defect detection characteristic for each illumination aperture position is determined based on the output beam detected for each aperture position. An optimum aperture configuration is determined based on the determined defect detection characteristic for each aperture position.

In a specific implementation, the aperture positions, at which an illumination aperture is each opened, comprise an array of grid points in the illumination pupil area. In a further aspect, opening a plurality of apertures at the plurality of aperture positions cause different incident angles. In yet another embodiment, in combination with any of these features, the defect detection characteristic is displayed as a defect graphical element that maps each aperture position of the pupil area to an image or signal that is generated from the output beam. In one aspect, the defect graphical element includes defect images that are arranged with respect to each other in a same way that the corresponding positions of the pupil area are arranged with respect to each other. In another implementation, the operation for opening an illumination aperture one at a time at each aperture position is performed by positioning a plurality of disks with respect to each other so that different aperture configurations from each disk are aligned with each other to produce a single aperture at each aperture position and the different aperture configurations are positioned within the pupil area and perpendicular to an optical axis of the incident beam.

In another embodiment, a defect detection characteristic for placement of an aperture at each of a plurality of combinations of two or more aperture positions is estimated based on a basis set of the defect detection characteristic that is determined for each aperture position, and the optimum aperture configuration is determined by determining which position or combination of positions has the most optimum defect detection characteristic. In a further aspect, estimating a defect detection characteristic for placement of an aperture at each of a plurality of combinations of two or more aperture positions is accomplished by adding the defect detection characteristic for each aperture position in the corresponding combination of two or more aperture positions. In another aspect, the defect detection characteristic for each aperture position comprises a defect-of-interest (DOI) image, a nuisance defect image, or a background image, and the defect detection characteristic for each of the plurality of combinations of two or more aperture positions is determined by adding the DOI image, nuisance image, or a background noise image for each aperture position from each combination of two or more aperture positions.

In one example, the optimum aperture configuration is not yet available on the inspection tool. In this case, the optimum aperture configuration may be manufactured and added to the tool. In example, the optimum aperture configuration is available on the inspection tool, the method further comprising using the optimum aperture configuration to inspect the sample for defects. In yet another aspect, the defect detection characteristic for each aperture position includes one or more of the following metrics: a defect-of-interest (DOI) image, a nuisance defect image, a background noise image, a DOI intensity value, a nuisance defect intensity value, a background noise intensity value, a DOI signal to noise ratio (SNR) value, a DOI signal to nuisance value, a DOI image texture value, a nuisance defect image texture value, a background noise image texture value, a DOI polarity value, a background noise polarity, an average DOI intensity value, an average nuisance defect intensity value, an average background noise value, number of DOIs detected, number of nuisance defects detected, ratio of number of DOIs and nuisance defects, etc.

In another embodiment, the invention pertains to an inspection system for inspecting a photolithographic reticle or wafer for defects. The system includes a light source for generating an incident beam, a configurable illumination pupil aperture for receiving the incident beam, an illumination optics module for directing the incident beam through the illumination aperture and onto a sample, a collection optics module for directing an output beam that is emitted from the sample in response to the incident beam, a sensor for detecting the output beam and generating an image or signal for the output beam, and a controller configured for (i) opening an illumination aperture of the illumination selector one at a time at each of a plurality of aperture positions of an illumination pupil area, wherein the aperture positions are spread across the illumination pupil area, (ii) while an illumination aperture is opened at each aperture position, causing the light source to direct an incident beam towards the illumination pupil area so as to selectively pass a corresponding ray bundle of the illumination beam at a corresponding set of one or more incident angles towards the sample and causing the sensor to detect an output beam emitted from the sample in response to the corresponding ray bundle of the incident beam impinging on the sample at the corresponding set of one or more incident angles, (iii) determining a defect detection characteristic for each aperture position based on the output beam detected for each aperture position, and (iv) determining an optimum aperture configuration based on the determined defect detection characteristic for each aperture position. The controller can also be configured for configuring a new aperture on the fly by combining apertures from multiple disks The controller can also be configured to perform any of the above described method operations.

In one aspect, the illumination selector does not include the optimum aperture configuration. In another aspect, the illumination selector does include the optimum aperture configuration, and the controller is further configured for setting the optimum aperture configuration on the illumination selector and using the system to inspect the sample for defects. In a specific implementation, the illumination selector comprises a plurality of disks that each have a plurality of aperture configurations, and an illumination aperture is opened one at a time at each aperture position by positioning the plurality of disks with respect to each other so that different aperture configurations from each disk are aligned with each other to produce a single aperture at each aperture position and the different aperture configurations are positioned within the pupil area and perpendicular to an optical axis of the incident beam. In other embodiments, the system comprises a plurality of light sources for generating a plurality of incident beams, and the illumination selector comprises a bundle of selectable fibers for directing each incident beam. In one aspect, the illumination selector does not include the optimum aperture configuration. In another aspect, the illumination selector does include the optimum aperture configuration, and the controller is further config- ured for setting the optimum aperture configuration on the illumination selector and using the system to inspect the sample for defects.

These and other aspects of the invention are described further below with reference to the figures.

DETAILED DESCRIPTION OF EXAMPLE EMBODIMENTS

Figure 1:
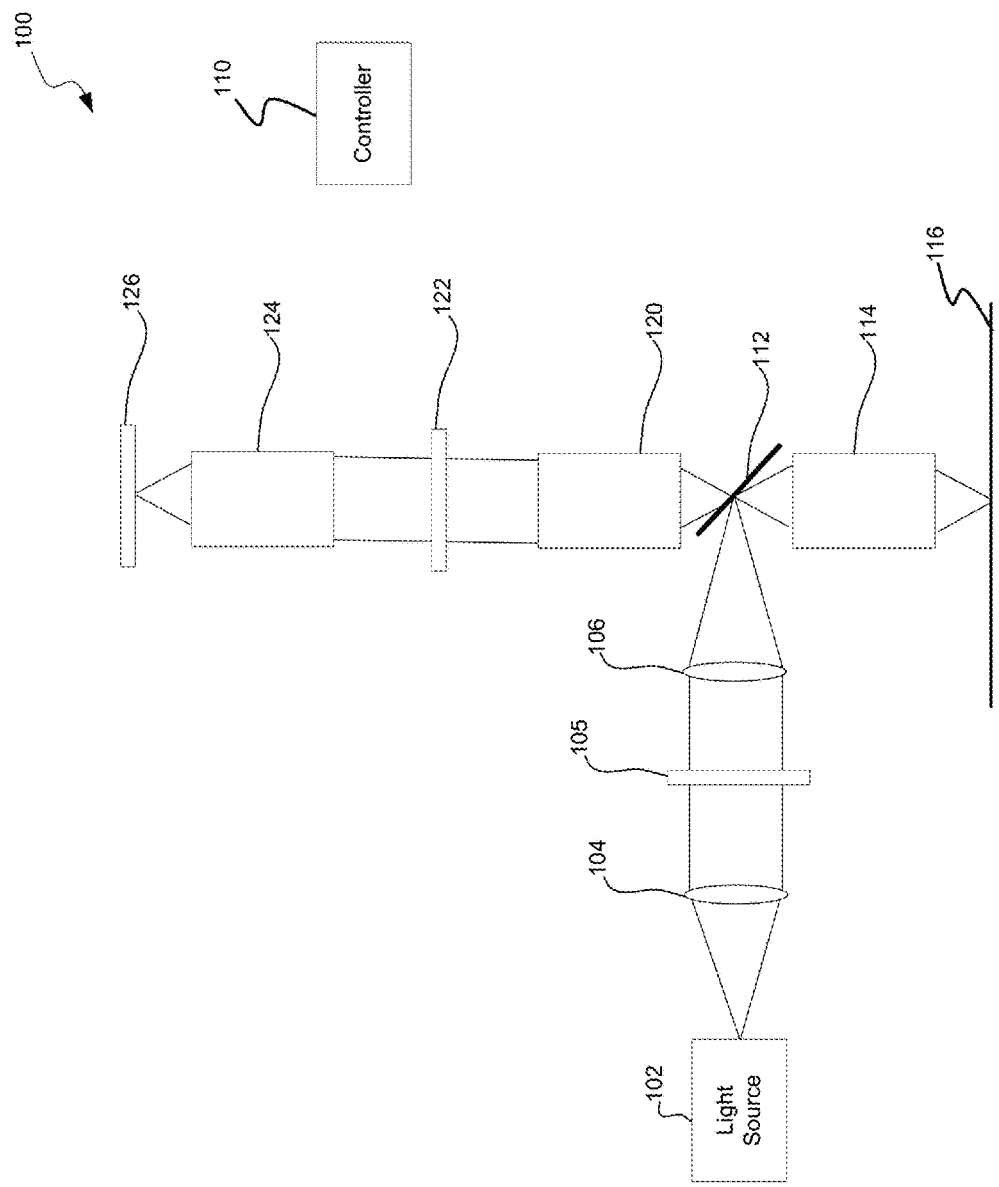
FIG. 1 is a diagrammatic representation of an example inspection apparatus.

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

Described herein are embodiments of inspection apparatus and methods for selecting and optimizing illumination pupil aperture configurations. Prior to describing specific embodiments for optimizing illumination pupil aperture configurations, general inspection systems will first be described. An inspection tool may include at least one light source for generating an incident light beam, a configurable illumination pupil aperture for receiving the incident beam, illumination optics for directing the incident beam through the illumination aperture and onto a sample, collection optics for directing an output beam that is emitted from the sample in response to the incident beam, a sensor for detecting the output beam and generating an image or signal for the output beam, and a controller for controlling the components of the inspection tool and facilitating the selection of one or more optimum illumination pupil aperture configurations as described further herein.

In the following exemplary inspection systems, the incident beam may be in any suitable form of coherent light. For instance, a laser having different wavelengths including deep ultra violet, ultra violet, or visible light wavelengths can be used. Different wavelengths can be used to optimize for detecting defects with different characteristics, and a combination of several wavelengths can be advantageous for further reducing laser coherence and averaging out the effect of wafer film thickness variations. A dark field inspection is preferably performed with a very bright light source so as to detect small defects on a sample by analyzing only the scattered light.

Additionally, any suitable lens arrangement may be used to direct the incident beam towards the sample and direct the output beam emanating from the sample towards a detector. The output beam may be reflected or scattered from the sample or transmitted through the sample. Likewise, any suitable detector type or number of detection elements may be used to receive the output beam and provide an image or a signal based on the characteristics (e.g., intensity) of the received output beam.

The illumination apparatus of the present invention are especially suitable for inspecting semiconductor devices or wafers, as well as reticles or masks. Other types of samples which may be inspected or imaged using the illumination apparatus of the present invention include any surface, such as a flat panel display.

FIG. 1 is a diagrammatic representation of an inspection system 100 in accordance with one embodiment of the present invention. As shown, the system may include a light source 102 for generating a brightfield incident beam, such as a broadband light source. Examples of brightfield light sources include a coherent laser light source, laser-driven light source, (e.g., deep UV or gas laser generator), a high-power plasma light source, a transillumination light source (e.g., halogen lamp), a filtered lamp, LED light source, etc. The inspection system may include any suitable number and type of light sources.

The incident beam from the light source then passes through a number of lenses which serve to relay (e.g., shape, focus, resize, magnify, reduce distortion, etc.) the beam towards a sample 116. In the illustrated embodiment, the incident beam passes through lens 104, which collimates the incident beam, and then through lens 106, which converges the incident beam. The incident beam is then received by beam splitter 112 that then reflects the incident beam through objective lens 114, which focuses the incident beam onto sample 116 at one or more incident angles.

The sample 116 may also be placed on a stage (not labeled) of the inspection system 100, and the inspection system 100 may also include a positioning mechanism for moving the stage (and sample) relative to the incident beam. By way of examples, one or more motor mechanisms may each be formed from a screw drive and stepper motor, linear drive with feedback position, or band actuator and stepper motor.

The inspection system 100 may also include an illumination selector 105 positioned at a pupil plane of the illumination beam. In one embodiment, the illumination selector 105 is in the form of a configurable pupil aperture that is adjustable to produce a plurality of different illumination beam profiles at the pupil plane. In a specific implementation, the illumination selector 105 can produce more than 25 different beam profiles. In yet another implementation, the illumination selector 105 can produce more than 100 different beam profiles. The inspection system 100 may also include one or more positioning mechanisms as described herein for selectively moving the different aperture configurations of the illumination selector into the path of the incident beam.

Figure 2:
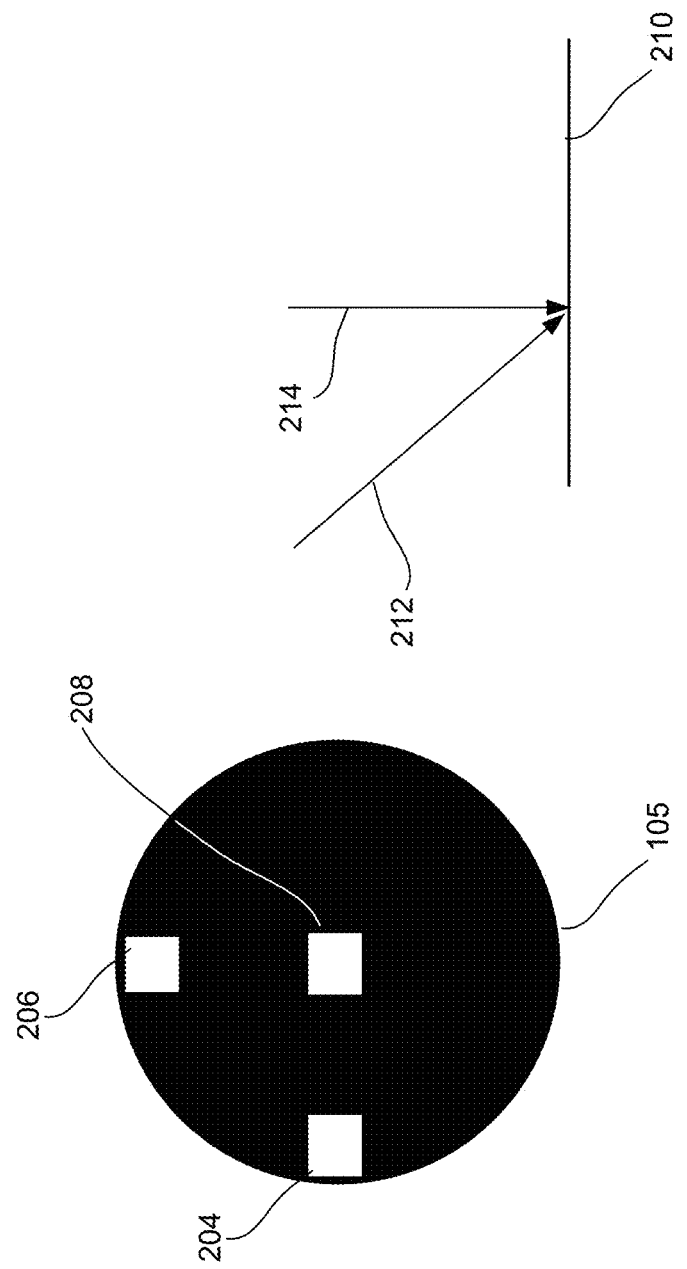
FIG. 2 illustrates different aperture configurations with respect to the incident beam that result in different incident angles.

In general, different illumination beam profile or aperture configurations result in different incident beam angles on the sample as described further herein. FIG. 2 illustrates different aperture configurations with respect to the incident beam 105 that result in different incident angles with respect to the normal axis for the incident beam impinging on a sample 210. Apertures closer to the center of the incident beam's pupil area result in lower incident angles from the normal axis, as compared with apertures that are positioned closer to the periphery of the incident beam's pupil area. For example, a center aperture 208 results in an incident beam 214 with a normal incident angle, while an outer aperture (204) results in an incident beam with a higher (or oblique) incident angle, such as 212.

After the incident beam(s) impinge on the sample 116, the light may then be reflected (and/or transmitted) and scattered from the sample 116, which is referred to herein as "output light" or an "output beam." The inspection system also includes any suitable lens arrangements for directing the output light towards one or more detectors. In the illustrated embodiment, the output light passes through beam splitter 112, Fourier plane relay lens 120, imaging aperture 122, and zoom lens 124. The Fourier plane relay lens generally relays the Fourier plane of the sample to the imaging aperture 122. The imaging aperture 122 may be configured to block portions of the output beams. For instance, the aperture 122 is configured to pass all of the output light within the objective numerical aperture in a bright field inspection mode, and configured to pass only the scattered light from the sample during a dark field inspection mode. A filter may also be placed at the imaging aperture 122 to block higher orders of the output beams so as to filter periodic structures from the detected signal.

After going through the imaging aperture 122, the output beam then passes through zoom lens 124 which serves to magnify the image of the sample 116. The output beam then impinges upon detector 126. By way of example, the detector may be in the form of a CCD (charge coupled device) or TDI (time delay integration) detector, photomultiplier tube (PMT), and other sensor.

The signals captured by the sensor 126 can be processed by a controller or computer system 110, which may include a signal processing device having an analog-to-digital converter configured to convert analog signals from the sensor into digital signals for processing. The controller 110 may be configured to analyze intensity, phase, and/or other characteristics of the sensed light beam. The controller 110 may be configured (e.g., with programming instructions) to provide a user interface (e.g., on a computer screen) for displaying resultant test images and other inspection characteristics as described further herein. The controller 110 may also include one or more input devices (e.g., a keyboard, mouse, joystick) for providing user input, such as changing aperture configuration, viewing detection results data or images, setting up a inspection tool recipe. In certain embodiments, the controller 110 is configured to carry out aperture selection or inspection techniques detailed below. Techniques of the present invention may be implemented in any suitable combination of hardware and/or software. The controller 110 typically has one or more processors coupled to input/ output ports, and one or more memories via appropriate buses or other communication mechanisms.

The controller 110 may be any suitable combination of software and hardware and is generally configured to control various components of the inspection system 100. For instance, the controller may control selective activation of the illumination sources 102, the illumination selector/aperture 105 settings, the imaging aperture 122 settings, etc. The controller 110 may also be configured to receive the image or signal generated by the detector 126 and analyze the resulting image or signal to determine optimum aperture configurations or whether defects are present on the sample, characterize defects present on the sample, or otherwise characterize the sample. For example, the controller may include a processor, memory, and other computer peripherals that are programmed to implement instructions of the method embodiments of the present invention.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

It should be noted that the above description and drawings are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

In general, certain embodiments of the present invention provide a way to quickly and comprehensively review different illumination pupil configurations (and corresponding different incident angles) in real-time on an inspection tool. In a specific implementation, detection results are correlated with specific illumination pupil aperture positions. For instance, the illumination pupil area is divided into a plurality of positions and an illumination aperture is opened one at a time for each pupil position. The pupil positions can be selected so that the variance of detection performance across the pupil can be determined. The pupil positions and corresponding apertures can be spread across the entire pupil so as to provide full angular coverage for the incident beam impinging on the sample. The pupil positions and corresponding apertures can have a relatively high resolution with respect to the pupil area. In a specific implementation, the pupil is divided into 40 grid points. In another implementation, the number of pupil positions is greater than 100. In yet another implementation, the number of pupil positions is greater than 200. Said in another way, the resolution of the illumination aperture per grid is higher with higher grid sampling.

The different aperture settings can be independent of each other. In one embodiment, the aperture configurations are positioned at different pupil locations that are unique and do not overlap so as to result in different angles of incidence. In another embodiment, some of the selected aperture configurations can depend on each other and have overlapping pupil locations.

Figure 3:
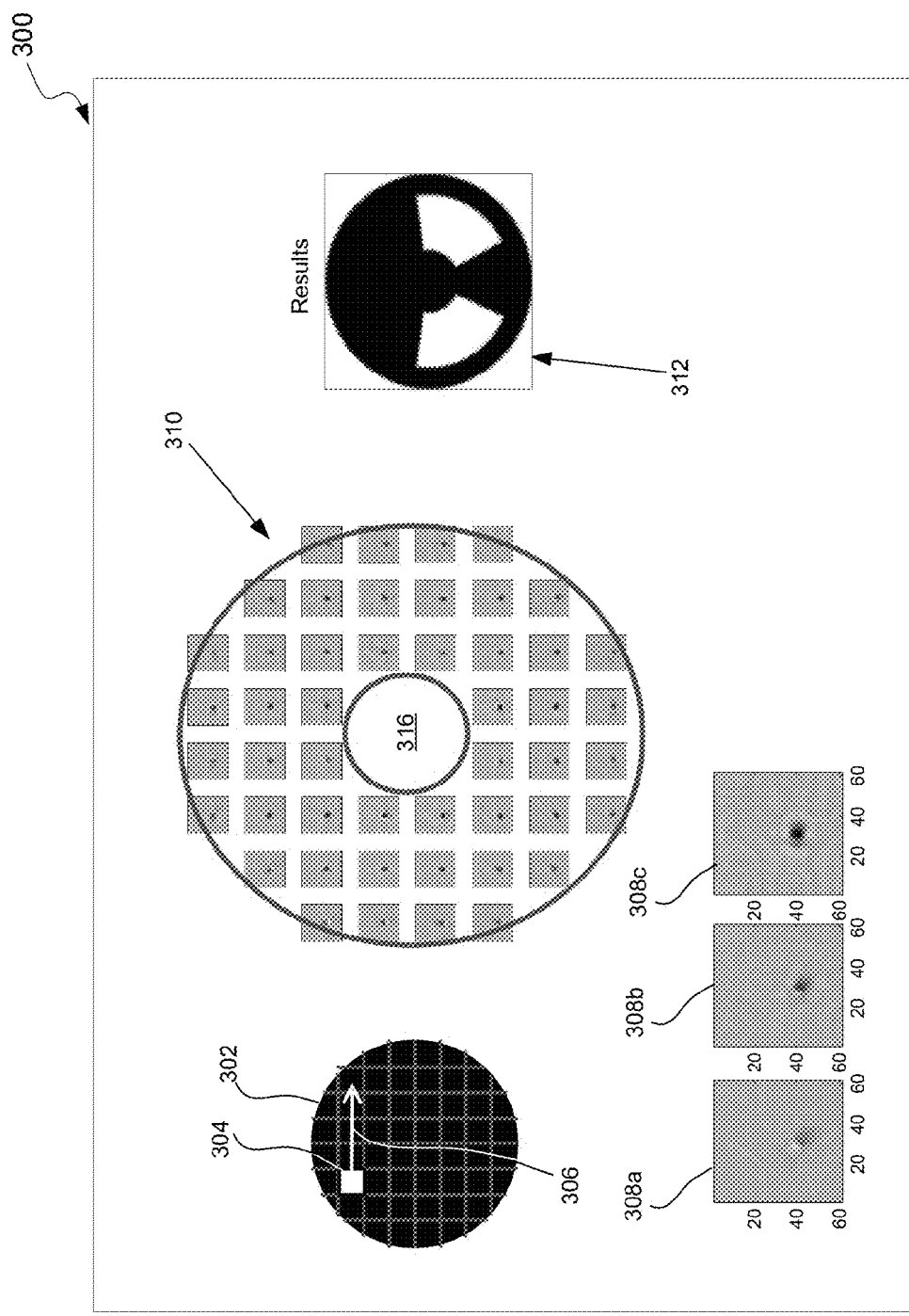
FIG. 3 represents a graphical user interface (GUI) that includes a view of defect detection performance for each grid position of an illumination pupil in accordance with one embodiment of the present invention.

FIG. 3 represents a graphical user interface (GUI) 300 that provides a view of defect detection performance for each grid position of an illumination pupil in accordance with one embodiment of the present invention. As shown, the GUI may include a pupil aperture element 302 that shows a current aperture position 304 with respect to the illumination pupil as the aperture position moves across the pupil, for example, in direction 306.

As each pupil aperture is individually opened, the GUI may also provide a detection graphical element 310 that maps each pupil position to particular detection results obtained from the inspection tool For instance, the detection graphical element 310 includes images that are arranged with respect to each other in the same way that the corresponding pupil aperture positions are arranged with each other. The detection graphical element 310 may also include an unobserved area 316 that corresponds to a particular pupil area from which detection results are not desired. For instance, the unobserved area 316 corresponds to a central portion of the pupil for which apertures were not applied potentially because of additional hardware blockage in the system.

As an aperture is opened at each pupil position, a smaller subset of corresponding thumbnails may be provided. As shown, the GUI 300 may also be configured to provide a thumbnail image that corresponds to the current pupil position (308), in addition to the most recently obtained thumbnail images (308a and 308b).

Figure 4:
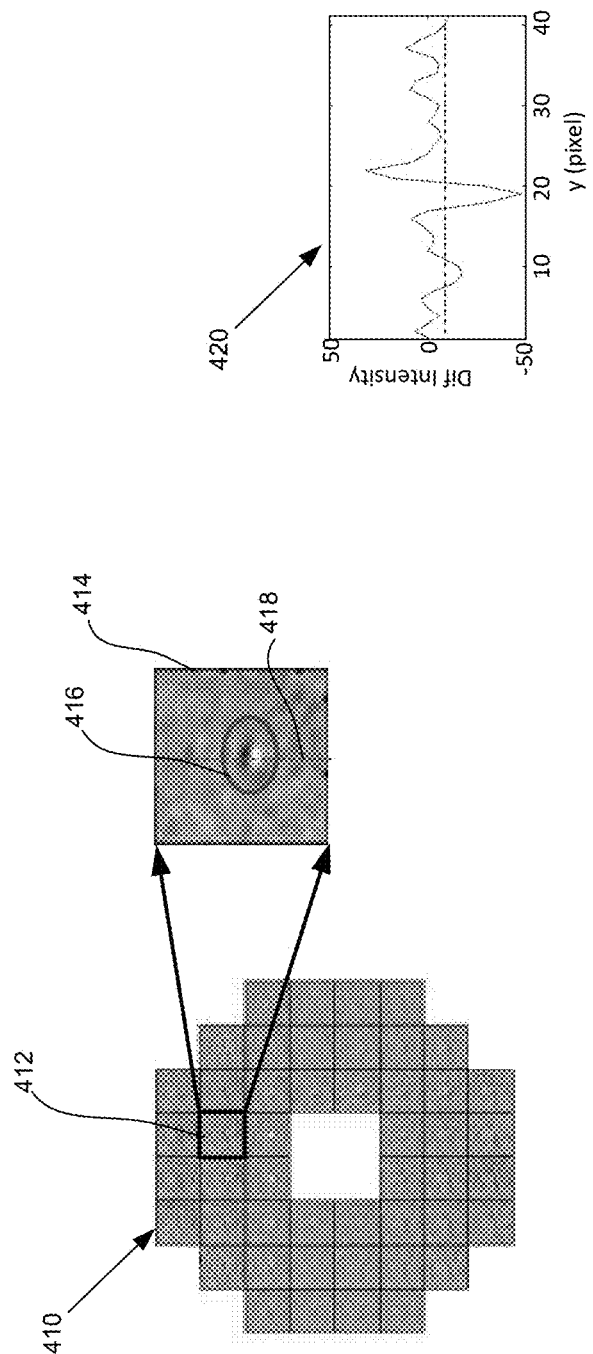
FIG. 4 illustrates review of results associated with a particular pupil aperture position in accordance with a specific implementation of the present invention.

The GUI 300 may also provide a mechanism for a user to review a particular set of results in more detail. FIG. 4 illustrates review of results associated with a particular pupil aperture position in accordance with a specific implementation of the present invention. As shown, a particular aperture position 412 of the illumination pupil 410 may be selected so as to open a higher resolution image 414 that includes defect 416 and was obtained with such aperture position. A graph 420 of the intensity as a function of sample position may also be displayed for the particular aperture position.

The detection images or signals for each aperture pupil position may be analyzed by a user or automatically to determine a set of aperture configurations that provide optimum detection results. For instance, the set of apertures that result in the highest contrast for a defect may be selected. An example optimum aperture configuration 312 is shown in FIG. 3.

Figure 5:
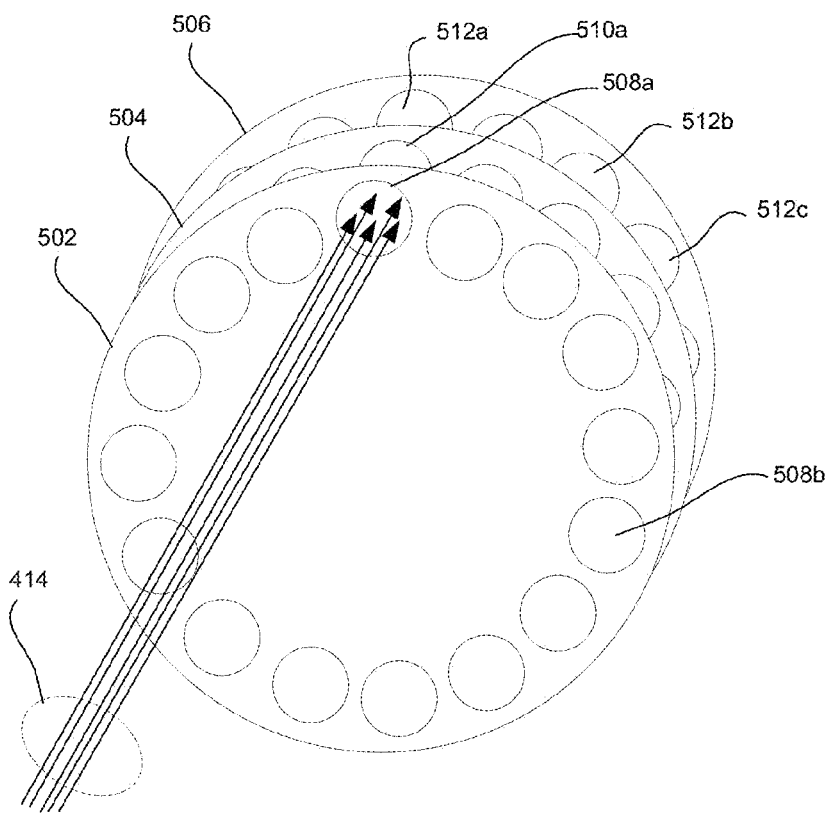
FIG. 5 is diagrammatic perspective view of an illumination selector in accordance with one embodiment of the present invention.

An illumination selector for selectively applying an aperture to each of a plurality of pupil positions may implemented by any suitable mechanism. In general, the illumination selector is configured to allow a ray bundle to individually pass through each position of the pupil and result in individual incident angles. FIG. 5 is diagrammatic perspective view of an illumination selector in accordance with one embodiment of the present invention. In this example, the illumination selector comprises three apertures disks 502, 504, and 506. Each aperture disk includes a plurality of different aperture configurations (e.g., aperture configurations 508a and 508b for disk 502, aperture configuration 510a for disk 504, and aperture configurations 512a, 512b, and 512c for disk 506). A particular aperture configuration for receiving the incident beam (or ray bundles) 414 can be selected for each disk and then the three selected aperture configurations from the three disks can then be overlaid to result in a diverse number of aperture settings and resulting illumination pupil profiles.

In general, each aperture configuration of each disk includes at least one transparent portion and may also include one or more opaque regions. For example, the transparent portions can be formed from any suitable transparent materials, such as glass, quartz, fused silica, etc., or each transparent region can merely be devoid of material so that light passes through each transparent portion of the aperture configuration. In contrast, each opaque portion blocks the corresponding spatial portion of the incident beam at the pupil plane, and each opaque portion is generally formed from an opaque material, such as chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide ($MoO_2$), tungsten oxide ($WO_2$), titanium oxide ($TiO_2$), or chromium oxide ($CrO_2$) may be formed over the opaque material. The shape of each aperture's transparent portion may be any suitable shape, such as rectangular, circular, elliptical, an lhcscreen (superposition of a circle and rectangle), marguerite (two lhc-screens, one rotated by 90°), rectellipse (superposition of an ellipse and rectangle), racetrack, etc. In general, an aperture configuration produces a particular incident beam profile, such as dipole, quadrapole, quasar, annulus, etc. In a specific example, Source Mask Optimization (SMO) or any pixelated illumination technique may be implemented. In the illustrated embodiment, each aperture configuration covers the entire illumination pupil area and is centered on the optical axis. However, an aperture configuration may alternatively be placed in a portion of the pupil area or at some other point (not pupil plane) along the optical path of the incident beam.

Figure 6A:
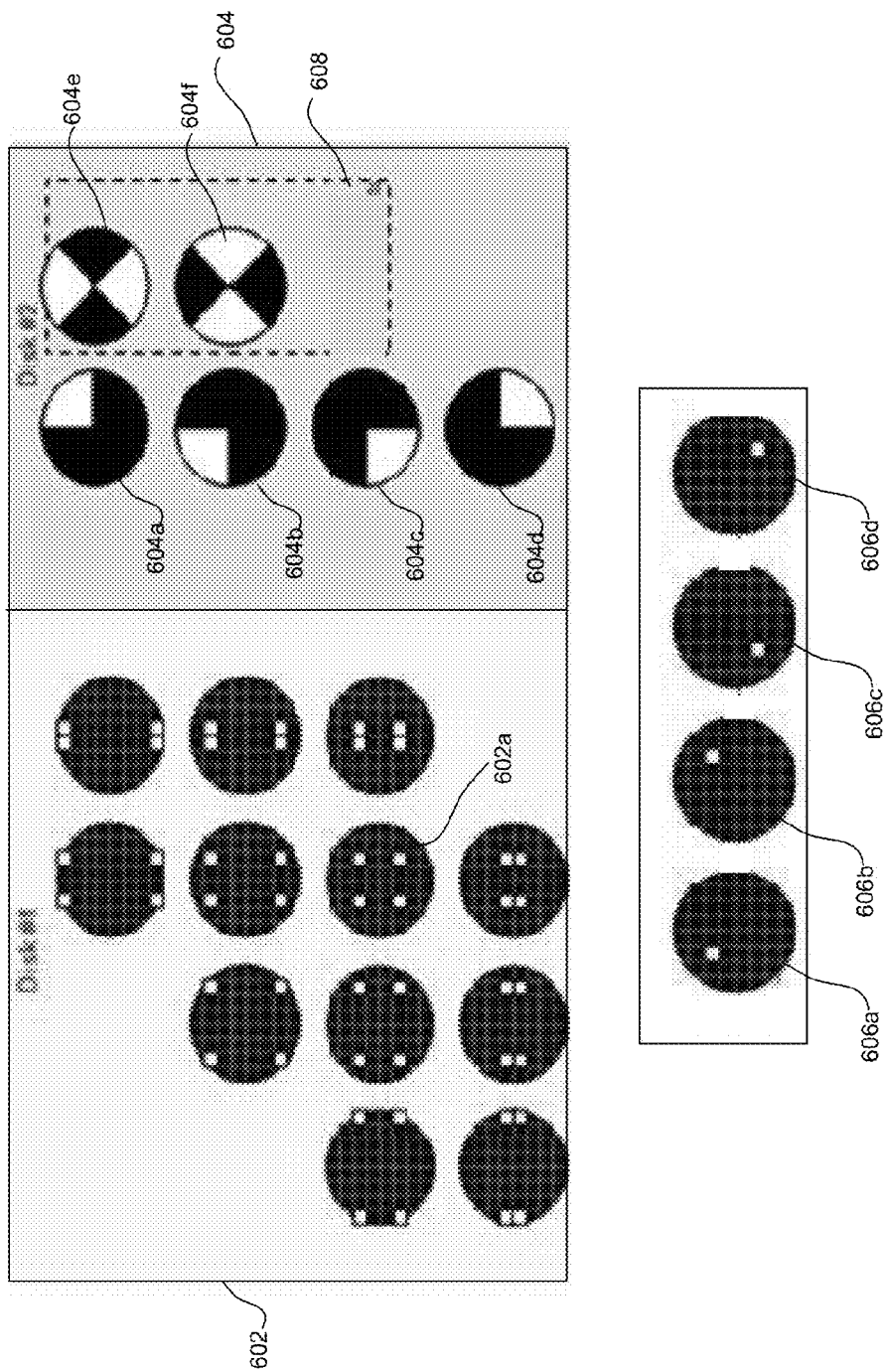
FIG. 6A illustrates combining specific aperture configurations to achieve different illumination configuration results in accordance with a specific example implementation of the present invention.

FIG. 6A illustrates combining specific aperture configurations to achieve different illumination configuration results in accordance with a specific example implementation of the present invention. As shown, a particular aperture configuration 602a is selected from a first disk 602 and combined one at a time with four aperture configurations 604a, 604b, 604c, and 604d of a second disk 604. The four different combinations result in aperture configurations 606a~606d. For instance, combining aperture configuration 602a from disk 602 with aperture 604a of disk 604 results in aperture configuration 606b. Likewise, combining aperture configuration 602a from disk 602 with aperture 604b of disk 604a. The illumination selector may include other aperture configurations on each disk (e.g., 604e and 604f) that may be combined with other aperture configurations from other disks for achieving an optimum set of apertures at more than one pupil position (not shown).

The results of using different aperture configurations can be utilized in any suitable manner, such as using the results to select one or more optimum configurations on the inspection tool or designing a new illumination pupil configuration so as to result in optimal incident angles performing inspection on the inspection tool. In a specific embodiment, the results for the individual aperture positions serve as a basis set that can be used to estimate the results for apertures at multiple positions.

Figure 6B:
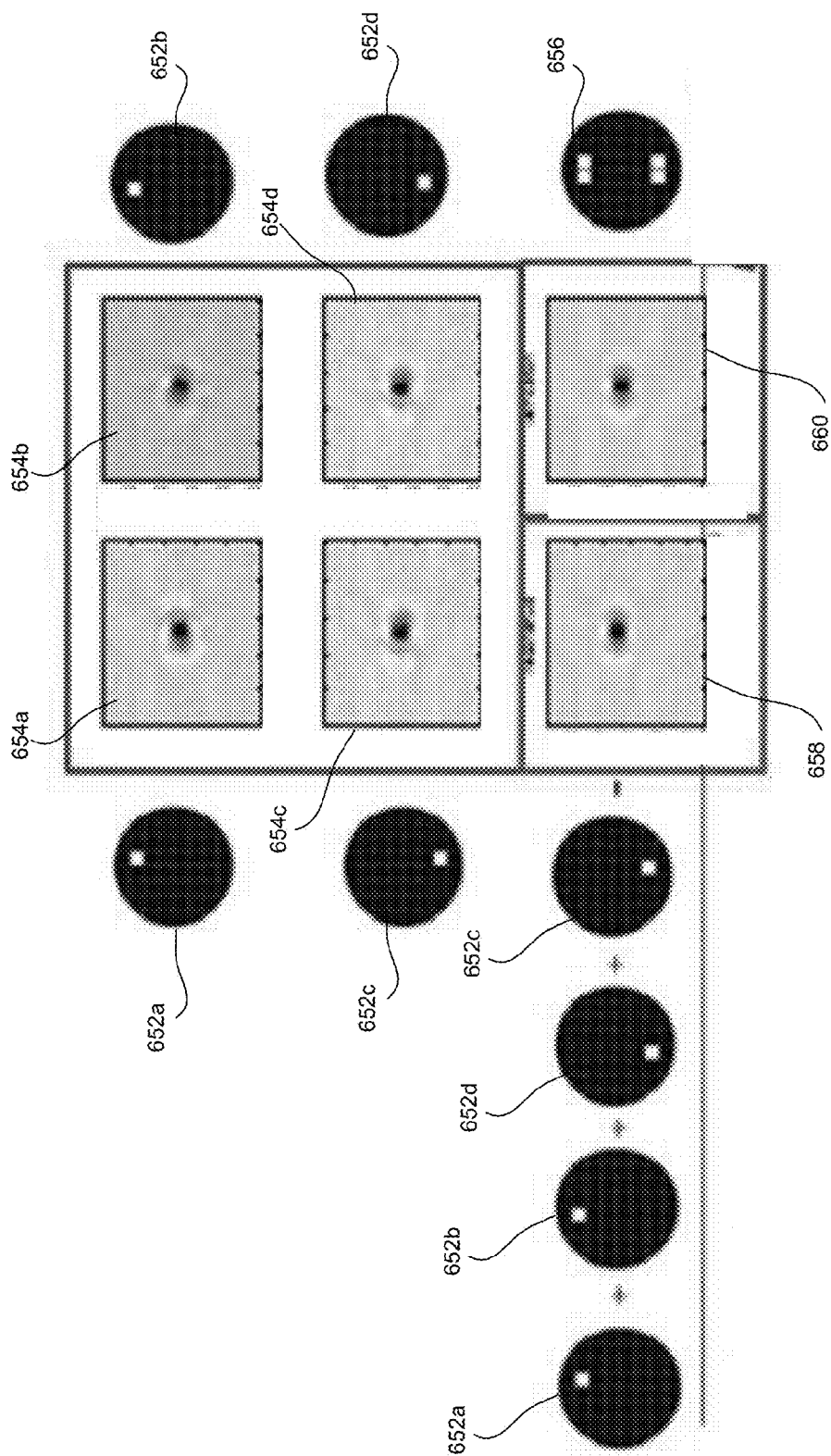
FIG. 6B illustrates estimating detection results of a particular aperture configuration based on the detection results obtained using a basis set of aperture configurations of an inspection tool in accordance with a specific example.

FIG. 6B illustrates estimating detection results of a particular aperture configuration based on the detection results obtained using a basis set of aperture configurations of an inspection tool in accordance with a specific example. For instance, four different images may be detected for an aperture placed at four different pupil positions. As shown, aperture configuration 652a results in image 654a; aperture configuration 652b results in image 654b; aperture configuration 652c results in image 654c; and aperture configuration 652d results in image 654d. Each aperture configuration has a single aperture at a single position so they are independent from each other.

The resulting images can be combined to estimate the results for apertures being placed at all four positions. Specifically, images 452a~452d that resulted from aperture configurations 652a~652d are added together to obtain an estimated image 658 for an aperture configuration having apertures at all four aperture positions (e.g., combination of 652a~652d). That is, image 658 is a reconstructed image or an estimate of the results that would occur with an aperture configuration 656. An actual image (e.g., image 660) for the combined pupil aperture positions can also be obtained if the corresponding configuration is also available on the inspection tool, for example, by selecting and overlaying different aperture configurations (e.g., from different disks) of the illumination selector. Otherwise, a new aperture configuration can be fabricated.

The aperture settings that are used to collect results from the inspection tool may also generally be used as a basis set for estimating results for additional aperture settings that are not currently available on the inspection tool. The estimation of results for a non-existing aperture setting can be determined without additional data collection or input, but simply based on the results from the basis set of aperture settings that are available on the inspection tool. Simulation is also not required for determining such estimated results and then selecting an optimized aperture configuration and accordingly, valuable intellectual property pertaining to a particular process may be protected and not revealed as part of a simulation process. This technique also saves significant amount of time by eliminating extensive simulation times.

The inspection tool can include a wide range of aperture settings that can be used for determining an optimum aperture configuration. As noted herein, some of the available aperture setting may be used as a basis set of independent aperture configurations (e.g., each aperture configuration corresponding to an individual aperture position in the illumination pupil) The inspection tool may also include other aperture configurations that are not independent from each other. In sum, the inspection tool may include any number of aperture configurations for determining optimum aperture configurations on the fly.

Figure 7:
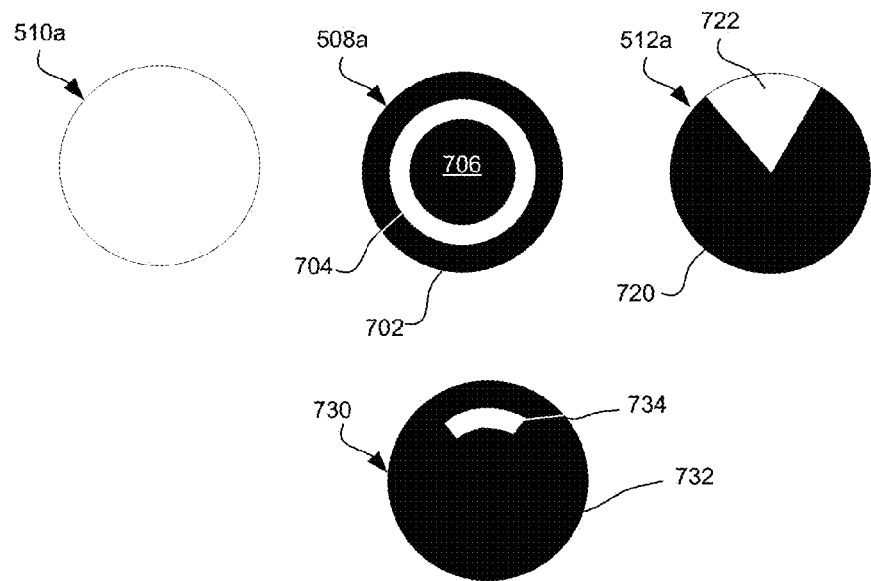
FIG. 7 illustrates combining three aperture configurations to achieve a first example of an aperture configuration.

The following examples illustrate only a small subportion of the diverse number of aperture configurations that may be achieved with certain embodiments of the present invention. These aperture configurations may be used to determine aperture configuration optimization, as well as other purposes. FIG. 7 illustrates combining three aperture configurations to achieve a first example of an aperture configuration. As shown, a first aperture configuration 510a selected from a first disk (504 of FIG. 5), a second aperture configuration 508a of a second disk (502), and a third aperture configuration 512a of a third disk (506) may be overlaid and combined to achieve a final aperture configuration 730 through which the illumination or incident beam (414) is passed, for example, at the pupil plane.

The first aperture configuration 510a does not include any blocking or opaque portions and, accordingly, lets the entire pupil area transmit ray bundles from the illumination beam. That is, all of the ray bundles in the pupil area pass through the first aperture 510a. The second aperture configuration 508a has an inner transparent ring 704, a center opaque portion 706, and an outer ring opaque portion 702. The third aperture configuration 512a has a transparent wedge portion 722 and an opaque portion 720 for the other wedges of pupil area. The resulting aperture configuration 730 has a transparent arc segment 734 that is surrounded by opaque portion 732.

Figure 8:
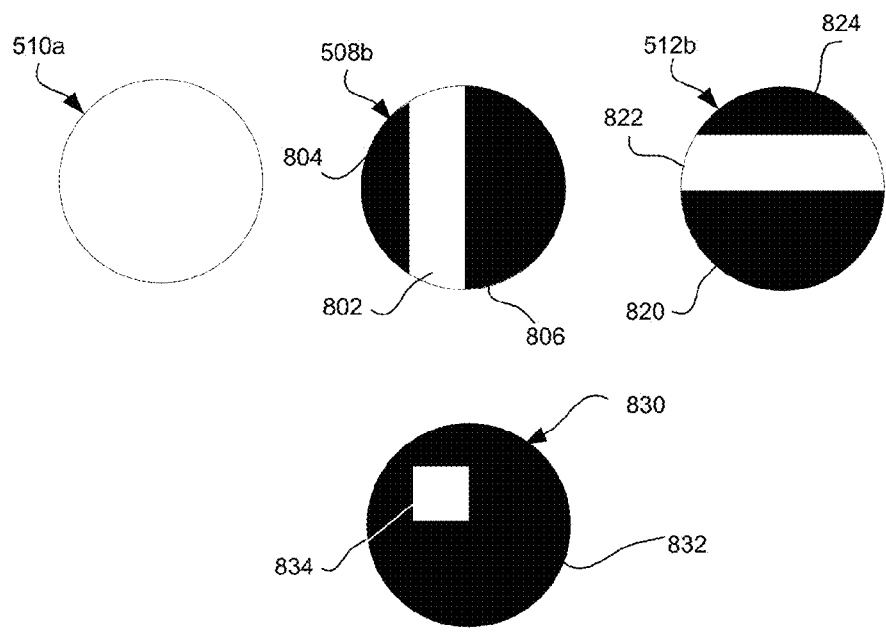
FIG. 8 illustrates combining three aperture configurations to achieve a second example of an aperture configuration.

FIG. 8 illustrates combining three aperture configurations to achieve a second example of an aperture configuration. Like FIG. 7, the first aperture configuration 510a is totally transparent over the entire pupil area. The second aperture configuration 508b of FIG. 8 has a transparent vertical transparent strip 802 surrounded by opaque portions 804 and 806. The third aperture configuration 512b has a horizontal transparent strip 822 surrounded by opaque portions 824 and 820. The resulting aperture configuration 830 has a square transparent portion 834 surrounded by opaque portion 832.

Figure 9:
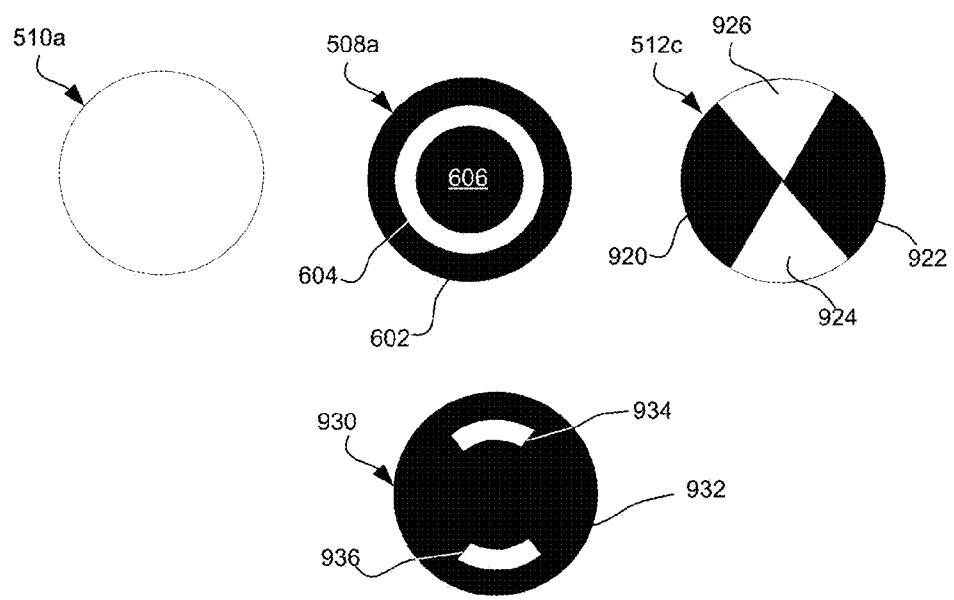
FIG. 9 illustrates combining three aperture configurations to achieve a third example of an aperture configuration.

FIG. 9 illustrates combining three aperture configurations to achieve a third example of an aperture configuration. The first aperture configuration 510a is totally transparent and the second aperture configuration 508a is identical to the aperture 508a of FIG. 7. The third aperture configuration 512c has transparent wedge portions 924 and 926 and opaque wedge portions 920 and 922. The resulting aperture configuration 930 has transparent arc segments 934 and 936 surrounded by opaque portion 932.

Figure 10:
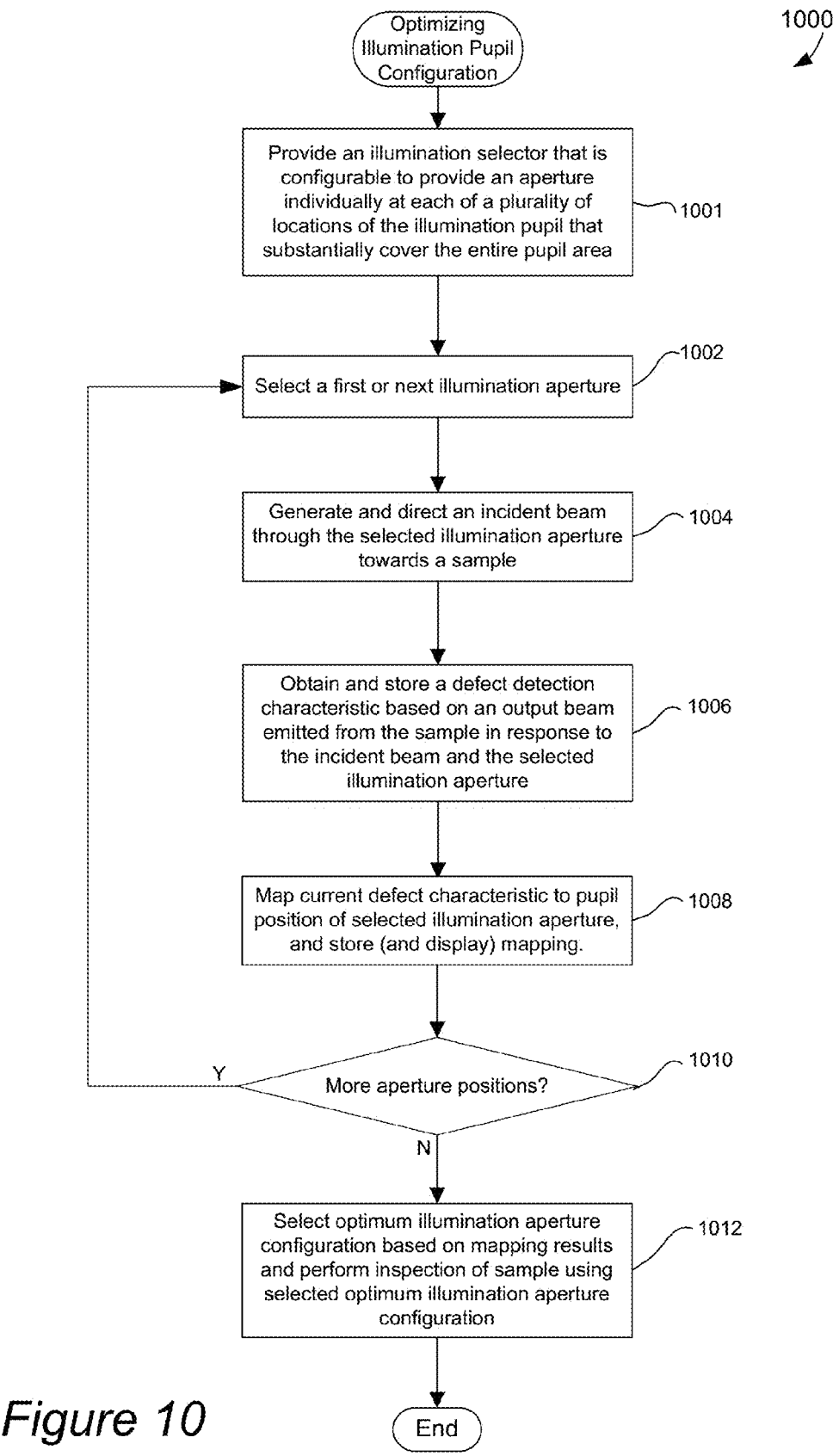
FIG. 10 is a flow chart illustrating a procedure for optimizing illumination pupil configuration in accordance with one embodiment of the present invention.

In certain embodiments, a basis set of aperture configurations can be used to test each aperture position with respect to the pupil area and then determine an optimum aperture configuration. Any suitable technique may be used to accomplish this goal. FIG. 10 is a flow chart illustrating a procedure 1000 for optimizing illumination pupil configuration in accordance with one embodiment of the present invention. As shown, an illumination selector that is configurable to provide an aperture individually at each of a plurality of locations of the illumination pupil is provided in operation 1001. In a specific implementation, the pupil locations substantially cover the entire pupil area.

A first one of the illumination apertures is selected in operation 1002. For instance, the illumination selector is configured so as to place an aperture at a first grid point of a pupil area that has been divided into an array of grid point locations that substantially cover the pupil area. An aperture configuration can be selected on each of the illumination selector's disks and the selected aperture configurations from the different disks are moved to be positioned within the pupil area and perpendicular to the optical axis of the incident beam.

An incident beam is then generated and directed through the selected illumination aperture towards the sample in operation 1004. For instance, the selected aperture position results in a ray bundle being transmitted towards the sample at one or more first angles of incident. For instance, the selected aperture results in the incident beam being directed towards the sample at a single incident angle or at a narrow range of incident angles, e.g., each selected aperture position can correspond to less than about 5 degrees of angles of incident.

Said in another way, different aperture configurations may be selected from different disks of the illumination selector, and these selected aperture configurations have different opaque and transparent portions in the pupil area. The selected aperture configurations can be overlaid with each other to cause a single aperture to be positioned at a particular grid point of the illumination pupil plane so that most of the incident beam is blocked going through the pupil area, except for a ray bundle corresponding to the single aperture at the particular grid point. The resulting incident beam will have an incident angle corresponding to the particular grid point of the pupil area. For example, if the aperture is placed as the outer edge of the pupil area, the incident beam will have a relatively oblique angle (e.g., see FIG. 2).

A defect detection characteristic may then be obtained and stored based on an output beam emitted from the sample in response to the incident beam and the selected illumination aperture in operation 1006. The defect detection characteristic may include any metric that can be measured or calculated based on an output beam from the same. Signal strength can generally correspond to intensity value. By way of specific examples, a defect detection characteristic can include defect-of-interest (DOI) signal strength, noise signal strength, and nuisance defect signal strength. A signal-to-noise ratio (SNR) and/or signal-to-nuisance ratio may also be determined. Each signal strength value may take the form of one or more of the following values pertaining to a real defect, nuisance defect, or noise: intensity value, image texture value, polarity (e.g., whether the defect or background flips from negative to positive values), etc. In alternative embodiments, a defect detection characteristic can take the form of more global variables, such as average DOI intensity, average nuisance defect intensity, average background noise for a large sample area, number of DOIs detected, number of nuisance defects detected, ratio of real and nuisance defects, etc.

The above defect detection characteristics can be obtained with respect to one or more of the following sample areas: a defect site, nuisance site, or background site. Any suitable technique can be used to define one or more defect, nuisance, or background sites on the sample under test. For example, a user can define defect, nuisance, and/or noise sites on the sample. Since the noise can be defined in terms of bulk noise, a noise characteristic can be obtained from surface roughness, edge roughness, die-to-die (or cell-to-cell or die-to-database) pattern variation with respect to the entire sample e.g., wafer.

In another example, a die-to-die (or cell-to-cell or die-to-database) comparison can be performed to obtain intensity differences between different die portions during an initial scan. The intensity differences that are above a predetermined threshold can be defined as defect sites. The signal strength at one or more of these defect locations can then be defined as a DOI signal strength characteristic. The defect intensity values for a set of defects can also be averaged together to obtain a DOI signal strength. The defect sites can also be identified during a previous inspection of a previous generation wafer.

A nuisance metric can be obtained by performing an initial scan on the sample to locate nuisance areas. In general, this scan can involve the inspection operator examining the wafer using the most general tool setting. The purpose of the initial scans is to identify potential defect/nuisance/background noise locations.

A noise metric may be determined by any number of techniques. For instance, the noise signal value can be defined as the standard deviation of the signal that is measured for the entire sample or the standard deviation of the signal that is measured in background areas of the sample. The background areas can be defined as areas that have not been determined to be defects. The defect detection characteristic may then be mapped to the pupil position of the selected illumination aperture and this mapping stored in operation 1008. The defect detection characteristic may also be displayed in association with the corresponding aperture position for the operator of the inspection tool. The pupil position at which the current aperture is positioned may be mapped with the resulting image and/or signal value for a particular DOI or set of DOI's (or nuisance or noise). The mapping can be displayed in any suitable manner so as to associate aperture position with a resulting defect detection characteristic, such as a DOI (or nuisance or noise) image or signal. Alternatively, the mapping between all of the aperture positions of the pupil area and their corresponding defect detection characteristic can be displayed after the images and signals are detected and collected by the inspection tool for all aperture positions.

After mapping is obtained for the current aperture position, it may then be determined whether there are any more aperture positions in operation 1010. For instance, the operations for obtaining images (or signals) may be repeated for each grid point of the illumination pupil area.

After the images and defect detection characteristic data has been collected for each pupil position in the illustrated embodiment, an optimum illumination aperture configuration may then be selected based on the mapping results in operation 1012. An optimum aperture configuration may be found by analyzing all of the collected defect detection data or images for each of the basis aperture positions, as well as all combinations of such basis aperture positions. For example, an aperture configuration that results (or is estimated to result) in a maximum DOI signal to noise ratio (SNR) value or a maximum DOI signal to nuisance defect ratio value may be selected as an optimum aperture configuration. An inspection of the sample may then be performed using the selected optimum illumination aperture configuration.

Any suitable technique may be implemented to analyze the images (or signals) from multiple aperture positions to select an optimum aperture configuration. In one embodiment, the images are reviewed by an operator who determines which images show a defect more clearly than other images. For instance, each combination of one or more aperture positions that produces a unique spatial signature for a defect of interest (DOI) can be selected as part of an optimum illumination aperture configuration.

In an automated embodiment, defect detection characteristic values can be added together for each combination of one or more illumination aperture positions. The combination that has an optimum combined result can then be defined as the optimum aperture configuration. For instance, image data for each aperture combination (from different incident angles) is added together to form a final combined image. Signal strength for each aperture combination can also be added together. Other types of image metrics, such as image texture, polarity, etc., can also be added together. In an alternative embodiment, the resulting metric for each aperture position may be analyzed individually to determine which individual metrics fall within a highest or lowest optimum range, and the aperture positions with the optimum metrics can all be defined together as a set of optimum aperture positions.

Certain embodiments provide an efficient way to determine an optimum aperture setting for an inspection tool. Certain embodiments of the present invention may also provide an aid to better understand DOI, nuisance, and background characteristics as a function of illumination angle. Additionally, detect characteristic data can be used as an engineering diagnostic tool to evaluate the optical performance across different illumination angles to provide solutions for tool matching problems.

In an alternative embodiment, the illumination pupil profile may be dynamically configured using a fiber bundle so as to determine an optimum illumination profile configuration. Several embodiments of such an apparatus are further described in U.S. Pat. No. 7,319,229, issued 15 Jan. 2008, by Vaez-Iravani et al., which patent is incorporated herein by reference in its entirety. In one aspect, the illumination apparatus includes a plurality of optical fibers for receiving one or more incident beam(s) and outputting such beam(s), a lens arrangement for receiving the beam(s) and directing the beam(s) towards a sample, and an illumination selector for transmitting one or more incident beams on selected ones of the fibers. In other words, different numbers of fibers may be selected to transmit different numbers of incident beams at different incident angles towards the sample. The illumination apparatus may also include a spatial coherence reduction mechanism for reducing speckle noise in the incident beams. In a specific implementation, the illumination apparatus may include a fiber modulator for altering a length of a portion of the fibers so as to reduce speckle noise. In other embodiments, the illumination pupil profile may be configured using a programmable aperture.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Accordingly, the present embodiments are to be considered as illustrative and not restrictive, and the invention is not to be limited to the details given herein.

What is claimed is:

1. A method of facilitating an inspection of a sample using an optical inspection tool, the method comprising:

opening an illumination aperture of an illumination selector one at a time at individual ones of a plurality of aperture positions of an illumination pupil area, wherein the aperture positions are spread across the illumination pupil area;

while each illumination aperture of the illumination selector is opened at each aperture position, directing an incident beam of the inspection tool towards the illumination pupil area and such illumination aperture manipulates the incident beam so as to selectively pass a corresponding ray bundle of the illumination beam at a corresponding set of one or more incident angles towards the sample;

while each illumination aperture is opened at each illumination aperture position, configuring an imaging aperture to pass only one or more ray bundles that are scattered from the sample in a dark field inspection mode;

while each illumination aperture is opened at each illumination aperture position, detecting the one or more ray bundles that are scattered from the sample and passed through the imaging selector;

determining a defect detection characteristic for each illumination aperture position based on the one or more ray bundles that are scattered from the sample;

estimating a defect detection characteristic for a plurality of combinations of two or more aperture positions of the illumination selector based on a basis set of the defect detection characteristic that is determined for each aperture position of the illumination selector and the one or more ray bundles that are scattered from the sample; and determining an optimum aperture configuration for the illumination selector based on which aperture position or combination of aperture positions has the most optimum defect detection characteristic that is determined or estimated from the one or more ray bundles that are scattered from the sample.

2. The method of claim 1, further comprising:

while each illumination aperture is opened at each illumination aperture position, configuring the imaging aperture to pass only one or more ray bundles that are reflected from the sample in a bright field inspection mode;

while each illumination aperture is opened at each illumination aperture position, detecting the one or more ray bundles that are reflected from the sample and passed through the imaging selector;

determining a defect detection characteristic for each illumination aperture position based on the one or more ray bundles that are reflected from the sample;

estimating a defect detection characteristic for a plurality of combinations of two or more aperture positions of the illumination selector based on a basis set of the defect detection characteristic that is determined for each aperture position of the illumination selector and the one or more ray bundles that are reflected from the sample; and determining an optimum aperture configuration for the illumination selector based on which aperture position or combination of aperture positions has the most optimum defect detection characteristic that is determined or estimated from the one or more ray bundles that are reflected from the sample.

3. The method of claim 1, wherein opening a plurality of illumination apertures at the plurality of aperture positions cause different incident angles.

4. The method of claim 1, further comprising displaying the defect detection characteristic as a defect graphical element that maps each aperture position of the pupil area to an image or signal that is generated from the detected one or more ray bundles.

5. The method of claim 4, wherein the defect graphical element includes defect images that are arranged with respect to each other in a same way that the corresponding positions of the pupil area are arranged with respect to each other.

6. The method of claim 1, wherein estimating a defect detection characteristic for placement of an illumination aperture at each of a plurality of combinations of two or more aperture positions is accomplished by adding the defect detection characteristic for each aperture position in the corresponding combination of two or more aperture positions.

7. The method of claim 6, wherein the defect detection characteristic for each aperture position comprises a defect-of-interest (DOI) image, a nuisance defect image, or a background image, and the defect detection characteristic for each of the plurality of combinations of two or more aperture positions is determined by adding the DOI image, nuisance image, or a background noise image for each aperture position from each combination of two or more aperture positions.

8. The method of claim 1, wherein the optimum aperture configuration is not yet available on the inspection tool.

9. The method of claim 1, wherein the optimum aperture configuration is available on the inspection tool, the method further comprising using the optimum aperture configuration for the illumination selector to inspect the sample for defects.

10. The method of claim 1, wherein the operation of opening an illumination aperture one at a time at each aperture position is accomplished by positioning a plurality of disks with respect to each other so that different aperture configurations from each disk are aligned with each other to produce a single illumination aperture at each aperture position and the different aperture configurations are positioned within the pupil area and perpendicular to an optical axis of the incident beam.

11. The method of claim 1, wherein the defect detection characteristic for each aperture position includes one or more of the following metrics: a defect-of-interest (DOI) image, a nuisance defect image, a background noise image, a DOI intensity value, a nuisance defect intensity value, a background noise intensity value, a DOI signal to noise ratio (SNR) value, a DOI signal to nuisance value, a DOI image texture value, a nuisance defect image texture value, a background noise image texture value, a DOI polarity value, a background noise polarity, an average DOI intensity value, an average nuisance defect intensity value, an average background noise value, number of DOIs detected, number of nuisance defects detected, ratio of number of DOIs and nuisance defects.

12. An inspection system for inspecting a photolithographic reticle or wafer for defects, comprising:

a light source for generating an incident beam;

a configurable illumination selector having a plurality of illumination apertures for receiving the incident beam;

an illumination optics module for directing the incident beam through the illumination selector and onto a sample;

a collection optics module for directing one or more ray bundles reflected or scattered from the sample to a configurable imaging selector;

the configurable imaging selector for passing one or more selected ones of the ray bundles reflected or scattered from the sample;

a sensor for detecting the one or more selected ray bundles that are passed through the imaging selector; and a controller that is configured to perform the following operations:

opening each illumination aperture of the illumination selector one at a time at individual ones of a plurality of aperture positions of an illumination pupil area, wherein the aperture positions are spread across the illumination pupil area;

while each illumination aperture is opened at each aperture position, causing the light source to direct an incident beam towards the illumination pupil area and such illumination aperture manipulates the incident beam so as to selectively pass a corresponding ray bundle of the illumination beam at a corresponding set of one or more incident angles towards the sample;

while each illumination aperture is opened at each illumination aperture position, configuring the imaging selector to pass only one or more ray bundles that are scattered from the sample in a dark field inspection mode;

while each illumination aperture is opened at each illumination aperture position, causing the sensor to detect the one or more ray bundles that are scattered from the sample and passed through the imaging selector;

determining a defect detection characteristic for each aperture position based on the one or more ray bundles that are scattered from the sample;

estimating a defect detection characteristic for each of a plurality of combinations of two or more aperture positions of the illumination selector based on a basis set of the defect detection characteristic that is determined for each aperture position of the illumination selector and the one or more ray bundles that are scattered from the sample; and determining an optimum aperture configuration for the illumination selector based on which aperture position or combination of aperture positions has the most optimum defect detection characteristic that is determined or estimated from the one or more ray bundles that are scattered from the sample.

13. The system of claim 12, wherein the controller is further configured for:

while each illumination aperture is opened at each illumination aperture position, configuring the imaging aperture to pass only one or more ray bundles that are reflected from the sample in a bright field inspection mode;

while each illumination aperture is opened at each illumination aperture position, causing the sensor to detect the one or more ray bundles that are reflected from the sample and passed through the imaging selector;

determining a defect detection characteristic for each illumination aperture position based on the one or more ray bundles that are reflected from the sample;

estimating a defect detection characteristic for a plurality of combinations of two or more aperture positions of the illumination selector based on a basis set of the defect detection characteristic that is determined for each aperture position of the illumination selector and the one or more ray bundles that are reflected from the sample, and determining an optimum aperture configuration for the illumination selector based on which aperture position or combination of aperture positions has the most optimum defect detection characteristic that is determined or estimated from the one or more ray bundles that are reflected from the sample.

14. The system of claim 12, wherein opening a plurality of illumination apertures at the plurality of aperture positions cause different incident angles.

15. The system of claim 12, wherein the controller is further configured for displaying the defect detection characteristic as a defect graphical element that maps each aperture position of the pupil area to an image or signal that is generated from the output beam.

16. The system of claim 15, wherein the defect graphical element includes defect images that are arranged with respect to each other in a same way that the corresponding positions of the pupil area are arranged with respect to each other.

17. The system of claim 12, wherein estimating a defect detection characteristic for placement of an illumination aperture at each of a plurality of combinations of two or more aperture positions of the illumination selector is accomplished by adding the defect detection characteristic for each aperture position in the corresponding combination of two or more aperture positions of the illumination selector.

18. The system of claim 17, wherein the defect detection characteristic for each aperture position comprises a defect-of-interest (DOI) image, a nuisance defect image, or a background image, and the defect detection characteristic for each of the plurality of combinations of two or more aperture positions is determined by adding the DOI image, nuisance image, or a background noise image for each aperture position from each combination of two or more aperture positions.

19. The system of claim 12, wherein the illumination selector does not include the optimum aperture configuration.

20. The system of claim 12, wherein the illumination selector does include the optimum aperture configuration, the controller further is configured for setting the optimum aperture configuration on the illumination selector and using the system to inspect the sample for defects.

21. The system of claim 12, wherein the illumination selector comprises a plurality of disks that each have a plurality of aperture configurations, and wherein an illumination aperture is opened one at a time at each aperture position by positioning the plurality of disks with respect to each other so that different aperture configurations from each disk are aligned with each other to produce a single illumination aperture at each aperture position and the different aperture configurations are positioned within the pupil area and perpendicular to an optical axis of the incident beam.

22. The system of claim 12, wherein the defect detection characteristic for each aperture position includes one or more of the following metrics: a defect-of-interest (DOI) image, a nuisance defect image, a background noise image, a DOI intensity value, a nuisance defect intensity value, a background noise intensity value, a DOI signal to noise ratio (SNR) value, a DOI signal to nuisance value, a DOI image texture value, a nuisance defect image texture value, a background noise image texture value, a DOI polarity value, a background noise polarity, an average DOI intensity value, an average nuisance defect intensity value, an average background noise value, number of DOIs detected, number of nuisance defects detected, ratio of number of DOIs and nuisance defects.

23. The system of claim 12, further comprising a plurality of light sources for generating a plurality of incident beams, wherein the illumination selector comprises a bundle of selectable fibers for directing each incident beam.

24. A method of facilitating an inspection of a sample using an optical inspection tool, the method comprising:

opening an illumination aperture one at a time at individual ones of a plurality of aperture positions of an illumination pupil area, wherein the aperture positions are spread across the illumination pupil area;

while an illumination aperture is opened at each aperture position, directing an incident beam of the inspection tool towards the illumination pupil area and such illumination aperture manipulates the incident beam so as to selectively pass a corresponding ray bundle of the illumination beam at a corresponding set of one or more incident angles towards the sample and detecting an output beam emitted from the sample in response to the corresponding ray bundle of the incident beam impinging on the sample at the corresponding set of one or more incident angles, wherein the illumination beam has a narrow or a broadband wavelength range;

determining a defect detection characteristic for each aperture position based on the output beam detected for each aperture position;

estimating a defect detection characteristic for placement of an aperture at each of a plurality of combinations of two or more aperture positions based on a basis set of the defect detection characteristic that is determined for each aperture position; and determining an optimum aperture configuration based on which aperture position or combination of aperture positions has the most optimum defect detection characteristic that is determined or estimated.

25. The method of claim 24, wherein:

the illumination beam is directed towards the sample at a plurality of different wavelength ranges, a defect detection characteristic is determined for each wavelength range and each aperture position, a defect detection characteristic is estimated for each wavelength range and placement of an aperture at each of the plurality of combinations of two or more aperture positions based on a basis set of the defect detection characteristic that is determined for each aperture position, and the optimum aperture configuration is determined based on which wavelength range and which aperture position or combination of aperture positions have the most optimum defect detection characteristic that is determined or estimated.

26. An inspection system for inspecting a photolithographic reticle or wafer for defects, comprising:

a light source for generating an incident beam having a narrow or a broadband wavelength range;

a configurable illumination pupil aperture for receiving the incident beam;

an illumination optics module for directing the incident beam through the illumination aperture and onto a sample;

a collection optics module for directing an output beam that is emitted from the sample in response to the incident beam;

a sensor for detecting the output beam and generating an image or signal for the output beam; and a controller that is configured to perform the following operations:

opening an illumination aperture of the illumination selector one at a time at individual ones of a plurality of aperture positions of an illumination pupil area, wherein the aperture positions are spread across the illumination pupil area;

while an illumination aperture is opened at each aperture position, causing the light source to direct an incident beam towards the illumination pupil area and such illumination aperture manipulates the incident beam so as to selectively pass a corresponding ray bundle of the illumination beam at a corresponding set of one or more incident angles towards the sample and causing the sensor to detect an output beam emitted from the sample in response to the corresponding ray bundle of the incident beam impinging on the sample at the corresponding set of one or more incident angles;

determining a defect detection characteristic for each aperture position based on the output beam detected for each aperture position;

estimating a defect detection characteristic for placement of an aperture at each of a plurality of combinations of two or more aperture positions based on a basis set of the defect detection characteristic that is determined for each aperture position; and determining an optimum aperture configuration based on which aperture position or combination of aperture positions has the most optimum defect detection characteristic that is determined or estimated.

27. The system of claim 26, wherein:

the light source is configured for generating an incident beam having a plurality of different wavelength ranges, a defect detection characteristic is determined for each wavelength range and each aperture position, a defect detection characteristic is estimated for each wavelength range and placement of an aperture at each of the plurality of combinations of two or more aperture positions based on a basis set of the defect detection characteristic that is determined for each aperture position, and the optimum aperture configuration is determined based on which wavelength range and which aperture position or combination of aperture positions have the most optimum defect detection characteristic that is determined or estimated.

* * * * *